United States Patent [19]

Gras

[11] Patent Number: 4,766,220

[45] Date of Patent: Aug. 23, 1988

[54] PROCESS FOR THE PREPARATION OF OPTICALLY ACTIVE ARYLOXYALKANOIC ACID COMPOUNDS

[75] Inventor: Georges Gras, Genay, France

[73] Assignee: Rhone-Poulenc Agrochimie, Lyons, France

[21] Appl. No.: 761,302

[22] Filed: Jul. 30, 1985

Related U.S. Application Data

[63] Continuation of Ser. No. 163,407, Jun. 26, 1980, abandoned.

[30] Foreign Application Priority Data

Jun. 29, 1979 [FR] France ................................ 79 17423

[51] Int. Cl.$^4$ .................... C07D 213/64; C07C 69/76; C07C 69/88
[52] U.S. Cl. .................................... 546/302; 546/301; 560/56; 560/61; 560/62; 562/466; 562/471; 562/472
[58] Field of Search .................. 546/301, 302; 560/56, 560/61, 62; 562/466, 471, 472

[56] References Cited

U.S. PATENT DOCUMENTS

| | | | |
|---|---|---|---|
| 3,378,582 | 4/1968 | Bolhofer | 560/61 |
| 3,454,626 | 7/1969 | Gottstein | 560/471 |
| 3,707,549 | 12/1972 | Mills | 560/61 |
| 4,055,595 | 10/1977 | Haydock et al. | 560/56 |
| 4,173,709 | 11/1979 | Metivier et al. | 562/471 |
| 4,310,689 | 1/1982 | Eveleens et al. | 562/472 |

FOREIGN PATENT DOCUMENTS

| | | | |
|---|---|---|---|
| 504M | 5/1961 | France | 562/471 |
| 1479271 | 12/1965 | France | 562/472 |

OTHER PUBLICATIONS

Gilman, Organic Synthesis, Coll. Vol. I, pp.-75-76, (John Wiley & Sons, New York, 1941).
Gilman, Organic Chemistry, vol. I, pp. 264-271, (John Wiley & Sons, New York, 1943).
Remick, Electronic Interpretations of Organic Chemistry, pp. 381-382, (John Wiley & Sons, New York, 1949).
Lowry, Mechanisms and Theory in Organic Chemistry, Harper and Row, New York, 1976, pp.-174-179).
March, Advanced Organic Chemistry, Reaction, Mechanisms and Structure, McGraw-Hill Pub., pp. 90-95, (1968).

Primary Examiner—Alan L. Rotman
Attorney, Agent, or Firm—Burns, Doane, Swecker & Mathis

[57] ABSTRACT

The invention relates to the preparation of optically active aryloxyalkanoic acid derivatives of the formula

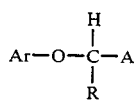

in which Ar represents an optionally substituted phenyl, naphthyl, phenoxy or pyridyloxy radical, R represents a $C_1$–$C_4$-alkyl radical and A represents a —$COOR_1$,

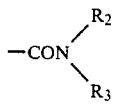

or —CO—Z radical, Z being halogen.

It consists in reacting an aqueous or aqueous-organic solution of an optically active alkali metal salt of a 2-halogeno-alkanoic acid with an aqueous solution of an alkali metal salt of the phenol of the formula Ar-OH at an elevated temperature under a pressure less than the vapor pressure of water at the chosen temperature.

It permits the preparation of aryloxyalkanoic acid derivatives with a very high content of the isomer having the D configuration, which can be used as herbicides.

22 Claims, No Drawings

PROCESS FOR THE PREPARATION OF OPTICALLY ACTIVE ARYLOXYALKANOIC ACID COMPOUNDS

This is a continuation of application Ser. No. 163,407, filed June 26, 1980, now abandoned.

The invention relates to a process for the preparation of optically active aryloxyalkanoic acids and of derivatives of such acids. More particularly, it relates to the preparation of aryloxyalkanoic acids, and derivatives of such acids, which have a very high content of the isomer possessing the D configuration, and which can be used as herbicides.

The optically active compounds which can be prepared in accordance with the process of the invention correspond to the general formula:

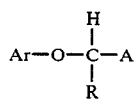  (formula I)

wherein:

Ar represents a monocyclic or bicyclic aromatic hydrocarbon radical of 6 to 10 carbon atoms (such as phenyl, naphth-1-yl or naphth-2-yl), the said radical being optionally substituted:
either by one to three substituents, which are identical or different and are chosen from amongst halogen (preferably chlorine) atoms and alkyl radicals of 1 to 4 carbon atoms (preferably methyl),
or by a phenoxy radical which is itself optionally substituted by 1 to 3 identical or different substituents chosen from amongst halogen (preferably chlorine) atoms, alkyl radicals of 1 to 4 carbon atoms (preferably methyl), the trifluoromethyl radical and the nitro radical,
or by a pyridyloxy radical which is itself optionally substituted by 1 to 3 substituents chosen from amongst halogen (preferably chlorine) atoms, alkyl radicals of 1 to 4 carbon atoms (preferably methyl) and the trifluoromethyl radical, A represents a $-COOR_1$,

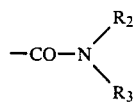

or $-COZ$ radical, wherein $R_1$ represents a hydrogen atom, one equivalent of a cation of an organic or inorganic base (e.g. one equivalent of a cation of an alkali metal or alkaline earth metal or of an optionally substituted ammonium cation) or an alkyl radical of 1 to 12 carbon atoms, which is optionally substituted by 1 or more halogen atoms or hydroxyl radicals, $R_2$ and $R_3$, which are identical or different, each represent a hydrogen atom or an alkyl radical of 1 to 6 carbon atoms which is optionally substituted by one or more OH, $NH_2$ or $C_1-C_4$-alkoxy, or $R_2$ and $R_3$ represent a phenyl radical which is optionally substituted by one or more halogens, or $C_1-C_4$-alkyl or $C_1-C_4$-alkoxy radicals, or $R_2$ and $R_3$ represent an alkenyl radical of 2 to 4 carbon atoms, Z represents a halogen atom (preferably chlorine), and R represents an alkyl radical of 1 to 4 carbon atoms (preferably methyl).

The invention more particularly relates to the preparation of the optically active aryloxyalkanoic acids, and salts of such acids, of the formula

  (formula II)

in which Ar and R have the same meaning as in the formula I and M represents an alkali metal cation (e.g. sodium or potassium) or a hydrogen atom.

The compound of the formula I and that of the formula II have an asymmetrically substituted carbon atom. Accordingly, each of these compounds can exist in two enantiomeric forms, of which one has the D absolute configuration and the other has the L absolute configuration. (According to another, equivalent, nomenclature, the letters R and S are sometimes used respectively in place of D and L in order to define the absolute configurations. In the text which follows, we shall systematically use the first of these nomenclatures, i.e. the letters D and L).

The compound of the formula I (or of the formula II) which contains equal proportions by weight of the isomer having the D absolute configuration and of the isomer having the L absolute configuration is the optically inactive racemic compound.

In the text which follows, the term optically active compound will be applied to a compound consisting predominantly (by weight) or completely of one of the isomers of this compound. The term optical purity of an optically active compound, that is to say of a compound consisting predominantly of one of the two isomers, will be used to mean the percentage by weight of the preponderant isomer contained in this compound. The term optically active compound of high optical purity will be applied to a compound in which the percentage by weight of the preponderant isomer is at least 90%.

It is known that numerous compounds corresponding to formulae I and II exhibit excellent herbicidal properties and that several of them are currently marketed for this use; these compounds especially include:

2-(2-methyl-4-chloro-phenoxy)-propionic acid (or Mecoprop), 2-(2,4,5-trichloro-phenoxy)-propionic acid (or Fenoprop), 2-(2,4-dichloro-phenoxy)-propionic acid (or Dichloroprop) and 2-(2-methyl-phenoxy)-propionic acid, these acids being generally marketed in the form of their sodium or potassium salts or of their amine salts or of their esters with lower alkanols, or 2-(α-naphthoxy)-N,N-diethylpropionamide (or Napropamide) and methyl 2-[4-(2,4-dichloro-phenoxy)-phenoxy]propionate (or Diclofop).

These compounds have hitherto generally been marketed in their racemic form. However, it has been observed that for several of the compounds mentioned above, one of the isomers exhibits a very much higher herbicidal activity, for the same dose, than that of the corresponding racemic compound. It thus appears very desirable to have available a process which makes it possible to prepare these herbicidal compounds in their optically active form, consisting predominantly, or completely, of the isomer exhibiting the better herbicidal activity. In the case of the herbicidal compounds mentioned above, it has been found that the isomer having the D configuration is responsible for almost the whole of the herbicidal activity, whilst the isomer having the L configuration exhibits virtually no herbicidal activity.

The invention thus relates more particularly to the preparation of the optically active derivatives of the compounds of the formulae I and II, the said derivatives consisting completely or predominantly of the isomer having the D configuration.

It has been proposed (French Pat. No. 1,479,271) to prepare the isomer, having the D configuration, of certain 2-phenoxy-propionic acids by reacting an alkali metal salt of 2-chloro-propionic acid, the salt being dextrorotatory in water, with an alkali metal salt of a phenol in the presence of an inert organic solvent of high boiling point, such as an aromatic hydrocarbon, at the boiling point of the solvent, and then acidifying the alkali metal salt thus obtained by treating it with a strong acid, so as finally to give D-2-phenoxy-propionic acid.

According to this process, the conversion of the alkali metal 2-chloropropionate to the alkali metal (D)-2-phenoxy-propionate takes place with a configuration inversion of the Walden inversion type.

The process claimed in this French patent makes it possible to obtain good yields of 2-phenoxy-propionic acids having a very high D isomer content. For practical purposes, using the technique described in the said patent, it is preferred to use anhydrous reactants and/or to remove the water present in the reaction mixture by azeotropic entrainment before starting the reaction.

Industrially, the use of anhydrous reactants presents serious disadvantages. It is expensive because it requires a prior dehydration of the reactants. Furthermore certain reactants, and in particular sodium 2-chloropropionate, are difficult to prepare in the anhydrous state.

Yet again, several of these anhydrous reactants are solids, which are difficult to use and which give heterogeneous reaction mixtures which are difficult to stir and are therefore of low reactivity.

Finally, the elimination of water by azeotropic entrainment requires the use of an auxiliary solvent which must subsequently be recovered and recycled.

The present invention proposes to overcome these disadvantages.

It is an object of the present invention to provide an improved process for the preparation of the optically active aryloxyalkanoic acids, and their derivatives, of the formulae I and II.

It is another object of the invention to make it possible to prepare these compounds from aqueous or aqueous-organic solutions of optically active alkali metal 2-halogeno-alkanoates, which are optionally prepared in situ.

It is another object of the invention to make it possible to prepare these compounds in excellent yield from an optically active alkyl 2-halogeno-alkanoate or from an optically active alkali metal 2-halogeno-alkanoate.

It is a further object of the invention to make it possible to obtain compounds having a high degree of optical purity.

It has now been found that these objects can be achieved in accordance with a novel process which forms the subject of the present invention.

This process is a process for the preparation of the optically active aryloxyalkanoic compounds corresponding to the formulae I and II, by the action of an optically active alkali metal salt of a 2-halogenoalkanoic acid, containing from 3 to 6 carbon atoms, on an alkali metal salt of a phenol of the formula Ar—OH  (formula III)

in which Ar has the same meaning as in the formula I, to give the alkali metal salt corresponding to the formula II, in which M represents an alkali metal cation, acidification of this salt to give the corresponding acid (the compound of the formula II for which M represents a hydrogen atom) and, optionally, subsequent conversion of this acid, in accordance with methods which are in themselves known, to any one of the compounds of the formula I. The process is characterised in that the alkali metal salt corresponding to the formula II is prepared by reacting the aqueous or aqueous-organic solution of the alkali metal salt of the 2-halogenoalkanoic acid with an aqueous solution of the alkali metal salt of the phenol at an elevated temperature under a pressure lower than the vapour pressure of water the reaction temperature.

The pressures referred to in the present application are absolute pressures, and the value zero corresponds to a complete vacuum.

The temperature to be used for this reaction can be selected in accordance with the reactivity of the alkali metal salt of the phenol of the formula III and of the alkali metal 2-halogeno-alkanoate used. It will, for example, be appreciated that this temperature will not necessarily be the same in the case of an alkali metal 2-chloropropionate as in the case of an alkali metal 2-bromopropionate, because these compounds have rather different reactivities.

The above temperature will be selected to be sufficiently high to allow the reaction to take place under satisfactory conditions, but it must remain below the temperatures at which the thermal degradation of the product or of the reactants employed in the reaction and possibly the autoracemisation of the optically active compounds becomes significant.

Where the above reaction is carried out using sodium 2-chloropropionate as the alkali metal 2-halogenoalkanoate, good results are obtained by working at between 70° and 160° C.

Preferably, the conditions used for carrying out the process according to the invention are those indicated below under a, b, c, d, e and f.

a. The 2-halogeno-alkanoic acid is 2-chloropropionic acid.

b. The alkali metal salts of the starting reactants used are, respectively, the sodium salt of 2-chloropropionic acid and the sodium salt of the phenol of the formula III, and hence the compound of the formula II, in which R represent a methyl radical and M represents a sodium atom, are obtained.

c. The reaction is carried out under a pressure less than or at most equal to atmospheric pressure and preferably of between 0.1 and 1 bar. The pressure chosen must be the lower, the lower is the reaction temperature which has been chosen. By way of example, if the reaction is carried out at 80°–90° C., this pressure must advantageously be of the order of 0.1 to 0.7 bar.

d. The aqueous or aqueous-organic solution of the alkali metal salt of the 2-halogeno-alkanoic acid is a highly concentrated solution, near the saturation limit.

When an organic solvent is used in addition to water, this solvent must be miscible with water and have a boiling point lower than the boiling point of water in the conditions of the reaction. Preferred solvents are chosen from amongst alcohols especially lower alcanols comprising one to four carbon atoms (e.g. methanol, ethanol).

If sodium 2-chloropropionate is used, this solution advantageously contains at least 20% by weight of sodium 2-chloropropionate, the remainder consisting of water and, optionally, an alcohol, e.g. a lower alkanol.

The upper limit of the amount of sodium 2-chloropropionate present in the solution corresponds to the saturation limit of sodium 2-chloropropionate of the solution under the temperature and pressure conditions used.

Advantageously, this solution contains from 20 to 50% by weight of sodium 2-chloropropionate.

e. The aqueous solution of the alkali metal salt of the phenol of the formula III is a solution of high concentration, near the saturation limit. It advantageously contains at least 50% by weight of the alkali metal salt of the phenol of the formula III. The upper limit of the amount of this salt used corresponds to the saturation limit of the solution under the temperature and pressure conditions used.

Preferably, a solution containing from 50 to 90% by weight of the sodium salt of the phenol of the formula III is used. The solution can be prepared by saponifying the phenol of the formula III with an industtrial aqueous sodium hydroxide solution. This solution is preferably concentrated to near its saturation limit by heating at a temperature of between 70° and 160° C. under a pressure lower than the vapour pressure of water at this temperature. Advantageously, this heating is carried out using the same temperature and pressure conditions as for the reaction according to the invention.

f. The alkali metal salt of the 2-halogenoalkanoic acid consists predominantly of the isomer having the L configuration (advantageously, it contains at least 90% of the L isomer). Because of the fact that the reaction according to the invention takes place with a Walden inversion, with a very slight reduction in the optical purity, compounds of the formulae I and II consisting predominantly of the isomer having the D configuration are thus obtained. (It is of course possible, where desired, to prepare compounds I and II consisting predominantly of the enantiomer having the L configuration by starting from an alkali metal salt of the 2-halogeno-alkanoic acid which is predominantly the D isomer).

The optically active alkali metal salt of the 2-halogeno-alkanoic acid, used as the starting material, can be prepared in accordance with a method which is in itself known, in a separate operation, by saponifying an optically active alkyl 2-halogeno-alkanoate with an inorganic base, such as sodium hydroxide solution. This alkali metal salt can also be prepared in situ, in accordance with a process which is in itself known (compare French Pat. No. 1,479,271), in which an alkyl 2-chloropropionate is run into the reaction mixture containing the phenol and an inorganic base, such as sodium hydroxide solution, whilst maintaining the temperature between 5° and 35° C. Where these conditions are used, it has been observed that an increase in temperature to above the values indicated previously results both in a very great lowering of the yield of alkali metal 2-chloropropionate, due to the formation of the alkali metal lactate, and in a rapid lowering of the optical purity of the alkali metal 2-chloropropionate formed. Since the saponification reaction is exothermic, it is thus necessary to cool the reaction mixture in order to maintain its temperature at between 5° and 35° C. throughout the duration of this reaction, and this is a serious disadvantage in the case of an industrial manufacturing process.

It has been found that, according to a variant of the process according to the invention, it is possible to carry out this preparation in situ of the optically active alkali metal salt of the halogenoalkanoic acid at an elevated temperature (above 40° C. and preferably between 70° and 160° C.) whilst completely avoiding the abovementioned disadvantages.

According to this variant of the process of the invention (which variant also forms part of the invention), the optically active alkali metal salt of the 2-halogenoalkanoic acid is prepared in situ in the reactor containing the aqueous solution of the alkali metal salt of the phenol of the formula III, at an elevated temperature (preferably between 70° and 160° C.), by introducing into this reactor, simultaneously and in substantially stoichiometric amounts, on the one hand an aqueous alkali metal hydroxide solution (preferably sodium hydroxide solution) and on the other hand an optically active alkyl 2-halogeno-alkanoate of the formula

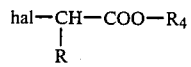   (formula IV)

in which hal represents a halogen atom, preferably chlorine, R has the same meaning as in formula I and $R_4$ represents a $C_1$-$C_6$-alkyl radical, under a pressure which is at one and the same time greater than the vapour pressure (or boiling pressure) of the alkyl 2-halogeno-alkanoate of the formula IV, and less than the vapour pressure of water at this temperature. By substantially stoichiometric amounts there are understood amounts such that the molar ratio of the two reactants introduced (sodium hydroxide solution and alkyl 2-halogeno-alkanoate) remains between 0.8 and 1.2 and is preferably above 1. Under these conditions it is found that though the temperature is high, there is virtually neither any formation of alkali metal lactate nor a reduction in the optical purity of the optically active compounds (such as the alkyl halogenopropionate and the alkali metal halogenopropionate) present in the reaction mixture and that the resulting product is obtained with excellent optical purity and in excellent yield.

For this variant, it is advantageous to use, as the starting reactants, on the one hand an aqueous sodium hydroxide solution near the saturation limit, and, on the other hand, an alkyl 2-halogeno-alkanoate of the formula IV, which consists predominantly of the isomer having the L configuration, is optically laevorotatory (the measurement being carried out in the absence of a solvent) and preferably contains at least 90% by weight of the L isomer. Thus, an aqueous organic solution of the optically active alkali metal salt of the halogenoalkanoic acid is obtained in situ, and this salt reacts, at the rate at which it is formed, with the alkali metal salt of the phenol, under the conditions indicated above.

To carry out this preparation of the alkali metal salts of the 2-halogeno-alkanoic acids in situ, the same temperature conditions can be used as in the process described above, for example temperatures of between 70° and 160° C.

The pressure to be used for this variant of the process according to the invention varies within limits which can be determined from the vaporisation diagrams of water and of the optically active alkyl 2-halogenoalkanoate used.

By way of indication, if methyl 2-chloropropionate is used and the process is carried out at 90° C., this pressure must be between 0.24 bar (the vapour pressure of methyl 2-chloropropionate at 90° C.) and 0.69 bar (the vapour pressure of water at 90° C.).

If it is desired to work under a lower pressure, it can be advantageous to replace the methyl 2-chloropropionate by a less volatile ester such as, for example, ethyl, propyl or butyl 2-chloropropionate.

The process according to the invention can be carried out discontinuously, as indicated in the examples. It can also be carried out continuously, by gradually running an aqueous or aqueous-alcoholic solution of the alkali metal 2-halogeno-alkanoate (or, in accordance with the other embodiment, gradually running the alkyl 2-halogeno-alkanoate and the sodium hydroxide solution) into the aqueous solution of the alkali metal salt of the phenol of the formula III, in accordance with the conditions indicated above, and removing the reaction product.

The process according to the invention provides, in the first instance, the alkali metal salts of the formula II, with M representing an alkali metal atom, and thereafter, by acidification of these salts, the corresponding free acids (the compounds of the formula II with M representing a hydrogen atom).

The various compounds of the formula I can be obtained from these acids and their salts in accordance with processes which are in themselves known:

acid halides of the formula I, in which A represents a COZ radical, can be obtained by reaction of these free acids with a halogenating agent such as $SOCl_2$, $PCl_5$ and $PCl_3$, from these acid halides, the corresponding amides (compounds of the formula I, in which A represents the

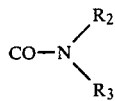

radical) can be prepared by reacting these acid halides with an amine of the formula $HNR_2R_3$, from these free acids or acid halides, it is possible to obtain esters (compounds of the formula I, in which A represents $COOR_1$ and $R_1$ represents an optionally substituted alkyl radical) by esterification by means of an appropriate alkanol.

Other esters can also be obtained by direct transesterification by means of an appropriate alkanol.

Certain salts of the free acids of the formula II are obtained in the course of the process of the invention (alkali metal salts and principally sodium and potassium salts). Other salts can be obtained from the free acids of the formula II by saponification with an appropriate inorganic or organic base.

The process according to the invention can be used for the preparation of the various optically active compounds corresponding to the formula I. It is very particularly suitable for the preparation of the following compounds in an optically active form having a very high content of the D isomer: 2-(2-methyl-4-chlorophenoxy)-propionic acid, 1-naphthoxy-propionic acid and 2-[4-(2,4-dichloro-phenoxy)-phenoxy]-propionic acid.

The examples which follow are described for the purpose of illustrating the invention, without however implying a limitation.

It will be noted from these examples that the process according to the invention makes it possible to obtain, from alkali metal 2-chloropropionates or alkyl 2-chloropropionates containing 98% of L isomer, 2-phenoxypropionic acids in which the content of D isomer is generally between 91.5 and 95.9%.

It will also be noted from these examples that the yield of phenoxypropionic acid in general remains between 96 and 98% if the starting material is sodium 2-chloropropionate and between 91 and 95% if the starting material is methyl 2-chloropropionate.

EXAMPLE 1

A 500 ml reactor equipped with a stirrer and an outlet tube followed by a condenser (thus making it possible to condense the vapours evolved) is used, the whole being connected to a system which makes it possible to work under reduced pressure.

2-Methyl-4-chloro-phenol (171 g, 1.2 mols) and an aqueous sodium hydroxide solution (92 g, comprising 44 g of sodium hydroxide and 48 g of water) are introduced into this reactor and the mixture is heated, with stirring, for 15 minutes at 90° C. under 0.25 bar (188 mm Hg).

An aqueous solution (200 ml) containing sodium 2-chloropropionate (130.5 g, 1 mol) having an optical rotation $[\alpha]_D^{20} = +3.90°$ (C=10, water) and water (125 g) is then run into the above mixture in the course of 2 hours 15 minutes, at a constant rate, whilst maintaining the temperature at 90° C. and the pressure at 0.25 bar. When all has been run in, the reaction mixture is kept at 90° C. and under 0.25 bar for 15 minutes, with stirring.

This mixture is then run into water (550 ml), after which it is acidified with 10 N HCl so as to bring it to pH 6. It is then washed with perchloroethylene (4×200 ml) and the phases are then separated. The aqueous phase is brought to pH 0.5 and the 2-(2-methyl-4-chloro-phenoxy)-propionic acid (hereafter referred to as MCPP acid) is reprecipitated and then extracted with perchloroethylene (2×300 ml). The organic phase is collected and then distilled under reduced pressure, giving MCPP acid (199.5 g, 0.93 mol) of 100% purity according to titration with alkali, i.e. a yield of 93% relative to the sodium 2-chloropropionate. 9.6 g of acid are recovered from the first organic phase separated off, thereby raising the total yield to 97%.

The MCPP acid obtained has an optical rotation $[\alpha]_D^{20} = +25.86°$ (C=10, acetone). On the basis of the theoretical optical rotation of optically pure (D) MCPP acid, measured under the same conditions, namely $[\alpha]_D^{20} = +28.15°$, The MCPP acid obtained consists of 95.9% of the D isomer, the remainder being L isomer, and its optical purity is thus 95.9%.

On the basis of the theoretical optical rotation of optically pure L sodium 2-chloropropionate, namely $[\alpha]_D^{20} = +4°$ (C=0.1 water), the sodium 2-chloropropionate used as the starting material consisted of 98% of the L isomer (the remainder being D isomer), and its optical purity was thus 98%.

Comparative experiment

The experiment described in Example 1 is carried out, using the same amounts of the same reactants and working under the same conditions, except that instead of working under 0.25 bar, the process is carried out under atmospheric pressure (1.013 bar), which is greater than the vapour pressure of water at 90° C. (0.69 bar). Under these conditions, the total yield of MCPP acid is 92% and its optical rotation is $[\alpha]_D^{20} = +20.8°$ (C=0.1 acetone), corresponding to an optical purity of 87%.

EXAMPLE 2

The process is carried out under the conditions described in Example 1, with only the following differences: the temperature is 150° C. (in place of 90° C.) and the pressure is 1.013 bar (760 mm Hg) in place of 0.25 bar. MCPP acid (205 g), of 100% purity according to titration with alkali is thus obtained, and a further amount of MCPP acid (2 g) is recovered from the first organic phase, separated off, making a total yield of 96.5%. Optical rotation $[\alpha]_D^{20} = +24.8°$ (C=0.1 acetone), corresponding to an optical purity of 94%.

EXAMPLE 3

The process is carried out under the conditions described in Example 2, with only the following difference: the temperature is 130° C. in place of 150° C. MCPP acid (200 g) is thus obtained and a further amount of this acid (9.5 g) is recovered from the first organic phase separated off, making a total yield of 97.6%. Optical rotation $[\alpha]_D^{20} = +24.52°$ (C=10, acetone), corresponding to an optical purity of 93.5%.

EXAMPLE 4

The process is carried out under the conditions described in Example 1, with only the following differences: the pressure is 0.26 bar (in place of 0.25 bar), and the aqueous solution of sodium 2-chloropropionate is replaced by an aqueous methanol solution consisting of sodium 2-chloropropionate (130.5 g, 1 mol), methanol, (42.0 g) and water (93.0 g).

MCPP acid (206 g) is thus obtained and a further amount of this acid (2.4 g) is recovered from the first organic phase separated off, making a total yield of 97.2%. $[\alpha]_D^{20} = +24.63°$ (C=10, acetone), corresponding to an optical purity of 93.7%.

The aqueous methanol starting solution was prepared in a separate operation, by treating methyl 2-chloropropionate (122.5 g), of $[\alpha]_D^{20} = -24.85°$ (in the absence of solvent), with an aqueous 30% strength sodium hydroxide solution (133 g, 1 mol) and methanol (10 g) at a temperature below 35° C., under normal pressure.

On the basis of the theoretical optical rotation of optically pure L methyl 2-chloropropionate, namely $[\alpha]_D^{20} = -27.8°$ (in the absence of solvent), the methyl 2-chloropropionate used as the starting material consisted of 94.7% of the L isomer (optical purity 94.7%).

EXAMPLE 5

The process is carried out under the conditions described in Example 4, with only the following differences: the temperature is 135° C. (in place of 90° C.) and the pressure is 1.013 bar (in place of 0.26 bar).

MCPP acid (a total of 208.4 g, total yield 91.7%) of optical rotation $[\alpha]_D^{20} = +24.0°$ (C=10, acetone), corresponding to an optical purity of 92.7%, is obtained.

EXAMPLE 6

The same device as in Example 1 is used. 2-Methyl-4-chlorophenol (171.5 g, i.e. 1.2 mols, taking into account that purity of 99.2%) and a 50% strength aqueous solution of sodium hydroxide (88 g, i.e. 1.1 mols) are introduced into the reactor and this mixture is heated to 90° C. under a pressure of 0.4 bar and is kept at this temperature and pressure for 20 minutes, with stirring.

The following are run simultaneously, in stoichiometric amounts, into this mixture: on the one hand, methyl 2-chloropropionate of 98.5% purity (124 g, i.e. 1 mol), having an optical rotation $[\alpha]_D^{20} = -25.3°$ (in the absence of solvent), and, on the other hand, a 50% strength aqueous solution of sodium hydroxide (80 g, i.e. 1 mol). The period over which the two reactants are run in is 1 hour. During the whole of this period, the temperature is kept at 90° C. and the pressure at 0.4 bar, and the reaction mixture is then kept at this temperature and this pressure for a further 30 minutes, with stirring.

This mixture is then run into water (550 ml); thereafter it is acidified with 10N HCl, so as to bring it to pH 5.5, and is washed with perchloroethylene (4×200 ml). The organic phase, which contains the excess of 2-methyl-4-chlorophenol and a small amount of MCPP acid, is separated off. The aqueous phase is acidified with 10N HCl to pH 0.5 and the 2-(2-methyl-4-chlorophenoxy)-propionic acid is reprecipitated and then extracted with perchloroethylene (2×300 ml). The organic phase is collected and then distilled under reduced pressure, and MCPP acid (200 g) having a purity of 99.6% determined by titration with alkali, and an optical rotation $[\alpha]_D^{20} = +24.2°$ (C=10, acetone) is obtained. A further amount of MCPP acid (1.7 g) is recovered from the first organic phase separated off.

Optical purity (or % content of D isomer) of the MCPP acid obtained: 92.8%.

optical purity (or % content of L isomer) of the methyl 2-chloropropionate starting material: 98.5%, and total yield of MCPP acid relative to methyl 2-chloropropionate: 94%.

EXAMPLES 7 TO 9

The procedure followed is as described in Example 6, starting from the same amounts of the same reactants, but varying the temperature and the pressure which are maintained whilst running in the methyl 2-chloropropionate and the aqueous sodium hydroxide solution, as well as varying the period over which these are run in. The results obtained are shown in the table below:

| Example No. | RUNNING-IN OF THE REACTANTS | | | MCPP ACID | |
|---|---|---|---|---|---|
| | Temperature (°C.) | Pressure (bars) | Period | Total yield, % | % of D isomer |
| 7 | 80 | 0.4 | 2 hrs | 92.5 | 92.7 |
| 8 | 90 | 0.4 | 1 hr 45 | 95.6 | 93.8 |
| 9 | 130 | 1.013 | 1 hr 20 | 93.0 | 91.5 |

EXAMPLE 10

The same device as in Example 1 is used. α-Naphthol (172.8 g, i.e. 1.2 mols) and a 50% strength aqueous solution of sodium hydroxide (88 g, i.e. 1.1 mols) are introduced into the reactor and this mixture is heated to 100° C. under 0.3 bar and is kept at this temperature and this pressure for 15 minutes, with stirring.

An aqueous methanol solution (265.5 g) of sodium 2-chloropropionate, having the same composition as in Example 4 and prepared as described in this example, from the same methyl 2-chloropropionate, is then run into the preceding mixture in the course of two hours. After all has been run in, the mixture is kept at 100° C. for 30 minutes.

Water (600 ml) is added to the mixture and the pH is brought to 5.5 by adding 10N HCl. The free naphthol is extracted with perchloroethylene (6×100 ml) at 85° C.

Perchloroethylene (500 ml) is added to the aqueous phase, which is kept at 85° C., before bringing the pH to 0.5 by adding 10N HCl. The organic phase is separated off and washed with hot water (2×100 ml), and the solvent is then removed by evaporation to constant weight in vacuo at 135° C.

This gives 1-naphthoxy-propionic acid (202 g) which melts at 125° C., is 99.8% pure according to titration with alkali, and has an optical rotation $[\alpha]_D^{20} = -39.2°$ (C=1, acetone). Yield 93.5%.

The optical purity of the compound obtained is increased by two successive recrystallisations from toluene, and 1-naphthoxy-propionic acid, having an optical rotation $[\alpha]_D^{20} = -45.6$ (C=1, acetone) and melting at 128° C., is thus obtained. A third recrystallisation does not increase the optical rotation and it is probable that the compound thus obtained consists entirely of the isomer having the D absolute configuration.

EXAMPLE 11

The same device as in Example 1 is used. 4-(2,4-Dichloro-phenoxy)-phenol (306 g, i.e. 1.2 mols) and a 50% strength aqueous sodium hydroxide solution (88 g, i.e. 1.1 mols) are introduced into the reactor and this mixture is heated at 90° C. under 0.3 bar for 1 hour.

The same aqueous methanol solution (265.5 g) of sodium 2-chloropropionate as in Example 4 is run into the above mixture in the course of 1 hour 30 minutes. When it has all been run in, the batch is kept at 90° C. for 30 minutes.

This mixture is then run into water (2,500 ml), and the pH is then brought to 6 by addition of 10N HCl. The mixture is washed with xylene (6×300 ml) and the phases are then allowed to separate. The aqueous phase is brought to pH 0.5 and 2-[4-(2,4-dichlorophenoxy)-phenoxy]-propionic acid precipitates and is extracted with xylene (2×300 ml). The organic phase is collected and then distilled under reduced pressure, and 2-[4-(2,4-dichloro-phenoxy)-phenoxy]-propionic acid (293 g, i.e. 0.896 mol), of 99.7% purity as determined by titration with alkali, is obtained; the yield is thus 89.6% relative to the methyl 2-chloropropionate starting material. A further amount of acid (14 g) is recovered from the first organic phase separated off (total yield: 93.9%).

The acid obtained has an optical rotation $[\alpha]_D^{20} = +15.6°$ (C=0.1, chloroform).

This acid (30 g) is dissolved in methanol (250 ml) and after addition of H₂SO₄ (0.5 ml) the mixture is heated at the boil for 2 hours whilst removing the water formed, and a part of the methanol, by distillation. Xylene (200 ml) is then added and the methanol is removed by distillation. The resulting solution of the ester in xylene is washed with an aqueous sodium bicarbonate solution in neutralise the H₂SO₄ and the unesterified acid. After removing the xylene by distillation under reduced pressure, methyl 2-[4-(2,4-dichloro-phenoxy)-phenoxy]-propionate (29 g) of optical rotation $[\alpha]_D^{20} = +26°$ (C=0.1, chloroform) is obtained, representing a yield of 92.7%.

What is claimed is:

1. In a process for preparing an optically active aryloxy-alkanoic acid compound of the formula:

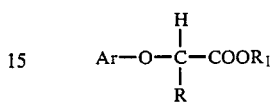

wherein:
Ar represents a monocyclic or bicyclic aromatic hydrocarbon radical of 6 to 10 carbon atoms which is optionally substituted by
(a) one to three substituents, which are identical or different and are chosen from amongst halogen atoms and alkyl radicals of 1 to 4 carbon atoms,
(b) a phenoxy radical which is optionally substituted by 1 to 3 identical or different substituents chosen from amongst halogen atoms, alkyl radicals of 1 to 4 carbon atoms the trifluoromet yl radical and the nitro radical, or
(c) a pyridyloxy radical which is optionally substituted by 1 to 3 substituents chosen from halogen atoms, alkyl radical of 1 to 4 carbon atoms and the trifluoromethyl radical,
$R_1$ represents a hydrogen atom, one equivalent of a cation of an organic or inorganic base or an alkyl radical of 1 to 12 carbon atoms, which is optionally substituted by 1 or more halogen atoms or hydroxyl radical, and
R represents an alkyl radical of 1 to 4 carbon atoms, by reacting an optically active alkali metal salt of a 2-halogenoalkanoic acid, of 3 to 6 carbon atoms, with an alkali metal salt of the phenol of the formula

in which Ar has the same meaning as above, to give an optically active alkali metal salt of the formula

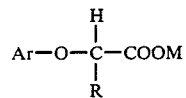

in which Ar has the same meaning as above and M represents an alkali metal cation, and then optionally, converting the alkali metal salt product to a corresponding optically active aryloxyalkanoic acid or ester, the improvement comprising:
preparing the alkali metal salt of the aryloxyalkanoic acid by reacting said optionally active alkali metal salt of 2-halogenoalkanoic acid with said alkali metal salt of phenol, in an aqueous or aqueous-organic solution at a temperature of about above 40° C. to about 160° C., under a pressure lower than the vapor pressure of water at the reaction temperature.

2. In a process for the preparation of an optically active aryloxyalkanoic acid compound of the formula:

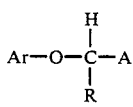

Ar represents a monocyclic or bicyclic aromatic hydrocarbon radical of 6 to 10 carbon atoms, the said radical being optionally substituted
by one to three substituents, which are identical or different and are chosen from amongst halogen atoms and alkyl radicals of 1 to 4 carbon atoms,
or by a phenoxy radical which is optionally substituted by 1 to 3 identical or different substituents chosen from amongst halogen atoms, alkyl radicals of 1 to 4 carbon atoms, the trifluoromethyl radical and the nitro radical,
or by a pyridyloxy radical which is optionally substituted by 1 to 3 substituents chosen from amongst halogen atoms, alkyl radicals of 1 to 4 carbon atoms and the trifluoromethyl radical,
A represents a $-COOR_1-$ radical, wherein:
$R^1$ represents a hydrogen atom, one equivalent of a cation of an organic or inorganic base or an alkyl radical of 1 to 12 carbon atoms, which is optionally substituted by 1 or more halogen atoms or hydroxyl radicals, and
R represents an alkyl radical containing from 1 to 4 carbon atoms, by reacting an optically active metal salt of a 2-chloroalkanoic acid, of 3 to 5 carbon atoms, with an alkali metal salt of a phenol of the formula

in which Ar has the same meaning as above, to give an optically active alkali metal salt corresponding to the formula

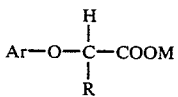

in which Ar and R have the same meaning as above and M represents an alkali metal cation, and then optionally, converting the alkali metal salt product to the corresponding optically active aryloxyalkanoic acid or ester, the improvement which comprises: preparing the alkali metal salt of the aryloxyalkanoic acid by reacting an aqueous or aqueous-organic solution of the optically active alkali metal salt of the 2-chloroalkanoic acid with an aqueous solution of the alkali metal salt of the phenol, at an elevated temperature of above about 40° C. to about 160° C., under a pressure lower than the vapor pressure of water at the reaction temperature.

3. A process according to claim 1, wherein the optically active alkali metal salt of 2-chloropropionic acid and the alkali metal salt of the phenol is a sodium salt.

4. A process according to claim 3, wherein the reaction between the sodium salt of the phenol and the optically active sodium salt of the chloropropionic acid is carried out at a temperature of between 70° and 160° C. under a pressure less than atmospheric pressure.

5. A process according to claim 4, wherein the pressure is between 0.1 and 0.7 bar.

6. A process according to claim 5, wherein the aqueous or aqueous-organic solution of optically active sodium chloropropionate consists of at least 20% by weight of sodium 2-chloropropionate.

7. A process according to claim 6, wherein the aqueous solution of the sodium salt of the phenol contains at least 50% by weight of this salt.

8. A process according to claim 7, wherein the optically active sodium 2-chloropropionate consists of at least 90% by weight of the isomer having the L configuration.

9. A process according to claim 1 in which Ar is said optionally substituted bicyclic aromatic hydrocarbon radical.

10. A process according to claim 9 in which 1-naphthoxy-propionic acid is prepared.

11. A process according to claim 1 wherein Ar represents a monocyclic or bicyclic aromatic hydrocarbon radical which may be optionally substituted by said optionally substituted phenoxy radical or by said optionally substituted pyridyloxy radical.

12. A process according to claim 1, in which Ar represents a monocyclic aromatic hydrocarbon radical which may be substituted by one to three substituents which are identical or different and are chosen from amongst halogen atoms and alkyl radicals containing from 1 to 4 carbon atoms.

13. A process according to claim 12 wherein the aqueous-organic solution of the alkali metal salt of the 2-chloroalkanoic acid is an aqueous-alcoholic solution.

14. The process according to claim 13 in which the optically active compound prepared is selected from a member of the group consisting of 2-(2-methyl-4-chloro-phenoxy)-propionic acid, 2-(2,4,5-trichlorophenoxy)-propionic acid, 2-(2,4-dichlorophenoxy)-propionic acid and 2-(2-methylphenoxy)-propionic acid.

15. The process according to claim 14, in which said optically active compound possesses the D configuration.

16. A process according to claim 1, wherein the 2-chloroalkanoic acid is 2-chloropropionic acid.

17. A process according to claim 2, wherein the 2-chloroalkanoic acid is 2-chloropropionic acid.

18. The process according to claim 1 in which methyl 2-[4-(2,4-dichlorophenoxy)-phenoxy]propionate is prepared.

19. The process according to claim 1 in which methyl 2-[4-(2,4-dichlorophenoxy)-phenoxy]propionate is prepared.

20. The process according to claim 12 wherein said optically active alkali metal salt of 2-chloroalkanoic acid is reacted with said alkali metal salt of phenol in an aqueous solution.

21. The process according to claim 1 wherein said optically active alkali metal salt of 2-chloroalkanoic acid is reacted with said alkali metal salt of phenol in an aqueous solution.

22. A process according to claim 2, wherein the optically active alkali metal salt of the 2-chloroalkanoic acid is prepared in situ in the reactor containing the aqueous solution of the alkali metal salt of the phenol, by introducing into this reactor, simultaneously and in substantially stoichiometric amounts, an aqueous solution of an alkali metal hydroxide and, an optically active alkyl 2-chloroalkanoate of the formula

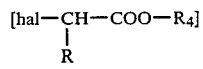
-continued
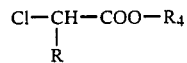
in which R has the same meaning as in claim 1 and $R_4$ represents an alkyl radical containing from 1 to 6 carbon atoms, at said elevated temperature, under a pressure less than the vapor pressure of water at said temperature and greater than the vapor pressure of the alkyl 2-chloropropionate at said temperature.
* * * * *